US007349522B2

(12) United States Patent
Yan et al.

(10) Patent No.: US 7,349,522 B2
(45) Date of Patent: Mar. 25, 2008

(54) DYNAMIC RADIATION THERAPY SIMULATION SYSTEM

(75) Inventors: Yulong Yan, Little Rock, AR (US); Xuejun Weng, Little Rock, AR (US); Vaneerat Ratanatharathorn, Little Rock, AR (US); Jose Penagaricano, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 402 days.

(21) Appl. No.: 11/158,489

(22) Filed: Jun. 22, 2005

(65) Prior Publication Data

US 2006/0291621 A1    Dec. 28, 2006

(51) Int. Cl.
*A61N 5/10* (2006.01)
(52) U.S. Cl. .................. 378/65; 378/95; 378/98.12
(58) Field of Classification Search .................. 378/65, 378/98, 95, 98.12
See application file for complete search history.

(56) References Cited

U.S. PATENT DOCUMENTS

| | | | |
|---|---|---|---|
| 4,994,965 A * | 2/1991 | Crawford et al. | ............. 378/95 |
| 6,621,889 B1 | 9/2003 | Mostafavi | |
| 6,690,965 B1 | 2/2004 | Riaziat et al. | |
| 6,697,452 B2 | 2/2004 | Xing | |
| 6,735,277 B2 | 5/2004 | McNutt et al. | |
| 6,740,402 B2 | 5/2004 | Tsukamoto | |

2004/0264640 A1 * 12/2004 Myles .................. 378/65

OTHER PUBLICATIONS

Nijmeijer et al., "Correction of lens-distortion for real-time image processing systems", VLSI SIgnal Processing, VI, 1993, pp. 316-324.*
Jaffray, D., et al., Managing Geometric Uncertainty in Conformal Intensity-Modulated Radiation Therapy, Seminars in Radiation Oncology, vol. 9, No. 1, pp. 4-19, Jan. 1999.
Yushkevich, P., et al., Towards Automatic, Model-Driven Determination of 3D Patient Setup Errors in Conformal Radiotherapy, MICCAI 98 Review Draft, University of North Carolina Computer Science Department Technical Report TR99-007, Chapel Hill, North Carolina, pp. 1-12, no later than 1999.
Chen, Q., et al., Fluoroscopic Study of Tumor Motion Due to Breathing: Facilitating Precise Radiation Therapy for Lung Cancer Patients, Med.Phys., vol. 28, No. 9, pp. 1850-1856, Sep. 2001.
Cosby, N., et al., Computer-Aided Radiation Therapy Simulation: Image Intensifier Spatial Distortion Correction for Large Field of View Digital Fluoroscopy, Phys. Med. Biology, vol. 43, pp. 2265-2278, 1998.

(Continued)

*Primary Examiner*—Chih-Cheng G Kao
(74) *Attorney, Agent, or Firm*—Ray F. Cox, Jr.

(57) ABSTRACT

A system for dynamic treatment simulation for radiotherapy. Software is implemented on a computer system to perform dynamic simulation by displaying every segment of dynamic treatment beams on top of real-time fluoroscopic image sequences. Automated distortion correction of the fluoroscopic image due to the image intensifier is performed in real-time. A respiration phase indicator measures changes in circumference of the patient's chest through the movement of a radio-opaque marker that appears directly in the fluoroscopic images of the patient.

4 Claims, 22 Drawing Sheets

OTHER PUBLICATIONS

Yan, Y., et al, PortSim™ Project Proposal, University of Arkansas for Medical Sciences, 6 pages, Oct. 4, 2002.

Bollet, M., et al., Can Digitally Reconstructed Radiographs (DRRS) Replace Simulation Films in Prostate Cancer Conformal Radiotherapy?, Int. J. Radiation Oncology Biol. Phys., vol. 57, No. 4, pp. 1122-1130, Nov. 15, 2003.

Gronenshield, E., Correction for Geometric Image Distortion in the X-Ray Imaging Chain: Local Technique Versus Global Technique, Med. Phys., vol. 26, No. 12, pp. 2602-2616, Dec. 1999.

Schueler, B., et al.,Correction of Image Intensifier Distortion for Three-Dimensional X-Ray Angiography, Proc. SPIE, vol. 2432, pp. 272-279, May 1995.

Fahrig, R., et al., Three-Dimensional Computed Tomographic Reconstruction Using a C-Arm Mounted XRII, Med. Phys., vol. 24, No. 7, pp. 1097-1106, Jul. 1997.

Rudin, S., et al., Accurate Characterization of Image Intensifier Distortion, Med. Phys., vol. 18, No. 6, pp. 1145-1151, Nov./Dec. 1991.

Chakraborty, D., Image Intensifier Distortion Correction, Med. Phys., vol. 14, No. 2, pp. 249-252, Mar./Apr. 1987.

Author Unknown, Varis Vision™, Using Xima Vision™, Varian Oncology Systems, United Kingdom, pp. 1-v1, 1-1-8-14 and 2 Cover Pages, Apr. 1998.

Author Unknown, RPM™ Real-Time Position Management, Respiratory Gating System Instructions for Use, Varian Oncology Systems, pp. 1-1-1-14 and Cover Page, Jul. 2002.

* cited by examiner

DYNAMIC RADIATION THERAPY SIMULATION SYSTEM

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to the simulation of radiation therapy and in particular, to a system which is able to simulate dynamic treatment regimes.

2. Brief Description of the Related Art

Fractionated conformal radiotherapy, such as intensity-modulated radiotherapy, that employs computer-controlled multi-leaf collimators, requires accurate beam placement in reference to the patient's anatomy. Beam placement and beam apertures are defined based on either CT simulation (beam's eye view planning) or conventional RF simulation. After the completion of the treatment plan, the treatment fields and their corresponding blocks (defined either by the multi-leaf collimator (MLC) or cerroband block) need to be verified prior to the treatment both for isocenter placement and for the shape of the MLC block. Currently, this check is done at the conventional simulator, which is not outfitted with an MLC. Consequently, the MLC pattern cannot be verified at the time of the port verification process prior to treatment. The aperture verification has to be repeated at the linac using a port imaging technique (port-film or electronic portal imaging device (EPID)). The drawbacks of this practice are that this process is not efficient as the filming has to be repeated several times, especially if shifts or corrections need to be applied; it does not allow for beam aperture verification at the conventional simulator; it can potentially increase the cost of treatment; and it can disrupt the patient's treatment schedule with unnecessary delays.

Varian Medical Systems, has a product that allows for the MLC shapes from a plan to be exported to the conventional simulator and to be visualized on top of a fluoroscopic static image. However, the Varian system cannot simulate dynamic treatment regimes.

It is therefore desirable to be able to project static and dynamic MLC plan images onto radiographic and fluoroscopic (RF) images for beam aperture verification prior to treatment.

It is also desirable to be able to simulate respiration-gated treatment regimes. In order to do so, it is necessary for simulation images to be correlated with the patient's respiratory cycle. U.S. Pat. No. 6,690,965 discloses a method and system for physiological gating for radiation therapy in which an optical or video image systems measures regular physiological movement of the patient's body. A gating signal is generated to suspend delivery of radiation upon certain threshold events detected in the physiological movement.

BRIEF SUMMARY OF THE INVENTION

The present invention is a dynamic treatment simulation system for forms of radiotherapy, such as intensity-modulated radiotherapy, that employ computer-controlled multi-leaf collimators (MLC) to shape and direct a beam of radiation to treat a particular field of a patient's anatomy. In order to accurately place the treatment fields in reference to the patient's anatomy, the treatment fields need to be verified prior to the treatment. Verification involves comparing actual fluoroscopic images of a patient with reference images, such as digitally reconstructed radiographs (DRR's) derived from the treatment plan.

The present invention combines both hardware and software. The primary hardware component, other than conventional computer systems, is a respiration phase indicator. The patient's respiration causes changes in the position and shape of the tumor and the surrounding tissue. By turning the beam on-and-off based on the phase of the patient's respiration cycle, a more accurate treatment of the tumor is possible. The respiration phase indicator of the present invention uses a belt about the chest of the patient to measure changes in the circumference of the chest. The changes in the circumference are indicated by linear changes in the position of a radio-opaque indicator. The respiration phase indicator of the present invention therefore differs from the prior art in that changes in circumference of the chest are measured rather than simple up-and-down movements of the chest and the indicator (since it is radio-opaque) appears directly in the fluoroscopic images of the patient.

The software component of the invention has a number of features that distinguish it from commercially-available systems. First, no known commercial system is capable of dynamic simulation. Dynamic simulation refers to treatment regimes where the beams vary in intensity, shape and orientation. Conventional simulation systems can only handle static treatment regimes. The present invention by contrast allows the display of every segment of dynamic treatment beams on top of real-time fluoroscopic image sequences. Further, a significant feature of the present invention is that of automated distortion correction of the fluoroscopic image. The fluoroscopic image of the patient is typically distorted in the image intensifier. The present invention is able to do real-time image distortion correction at 30 frames per second. The capability of real-time image distortion correction is critical to the ability to do dynamic simulations.

Displaying each segment of dynamic treatment beams on top of real-time fluoroscopic image sequences allows the physician-physicist team to verify that all beamlets are aiming at right target prior to real treatment. To address the movement of tumors and surrounding tissues due to respiration, the respiration cycle indicator allows the simulation of respiratory gated IMRT treatment. Automated distortion correction of image intensifier and image registration enable more accurate image comparison. The present invention can overlay reference images, contours, block and MLC ports on the fluoroscopic image. It can help position the patient by fusing reference images with the real-time fluoroscopic image. It can acquire sequential simulation images for a number of respiratory cycles to study organ motion and determine the size of the margin. It can also do filmless simulation with the help of DICOM connectivity.

These and other features, objects and advantages of the present invention will become better understood from a consideration of the following detailed description of the preferred embodiments and appended claims in conjunction with the drawings as described following.

BRIEF DESCRIPTION OF THE SEVERAL VIEWS OF THE DRAWINGS

FIG. 5 is a series of views showing rendering styles for image comparison in the Review Workspace.

FIG. 6 represents a series of online image comparison rendering styles in the Monitor Workspace (full screen mode) while simulating the patient.

In FIG. 10B, an artificial grid is displayed.

DETAILED DESCRIPTION OF THE INVENTION

With reference to FIGS. 1-14, the preferred embodiment of the present invention may be described.

The ideal goal of image-guided high-precision radiation therapy is to deliver a highly conformal dose to even a moving tumor while sparing surrounding normal tissues. Such a goal is becoming more practical with the merging of treatment planning technologies based on four-dimensional CT, tumor tracking technologies and respiration gating systems. Consequently new treatment simulation systems are needed to accommodate changes in treatment planning and delivery of four-dimensional image guided radiation therapy (4DIGRT) and respiration-gated intensity-modulated radiation therapy (RGIMRT).

Figure 8:
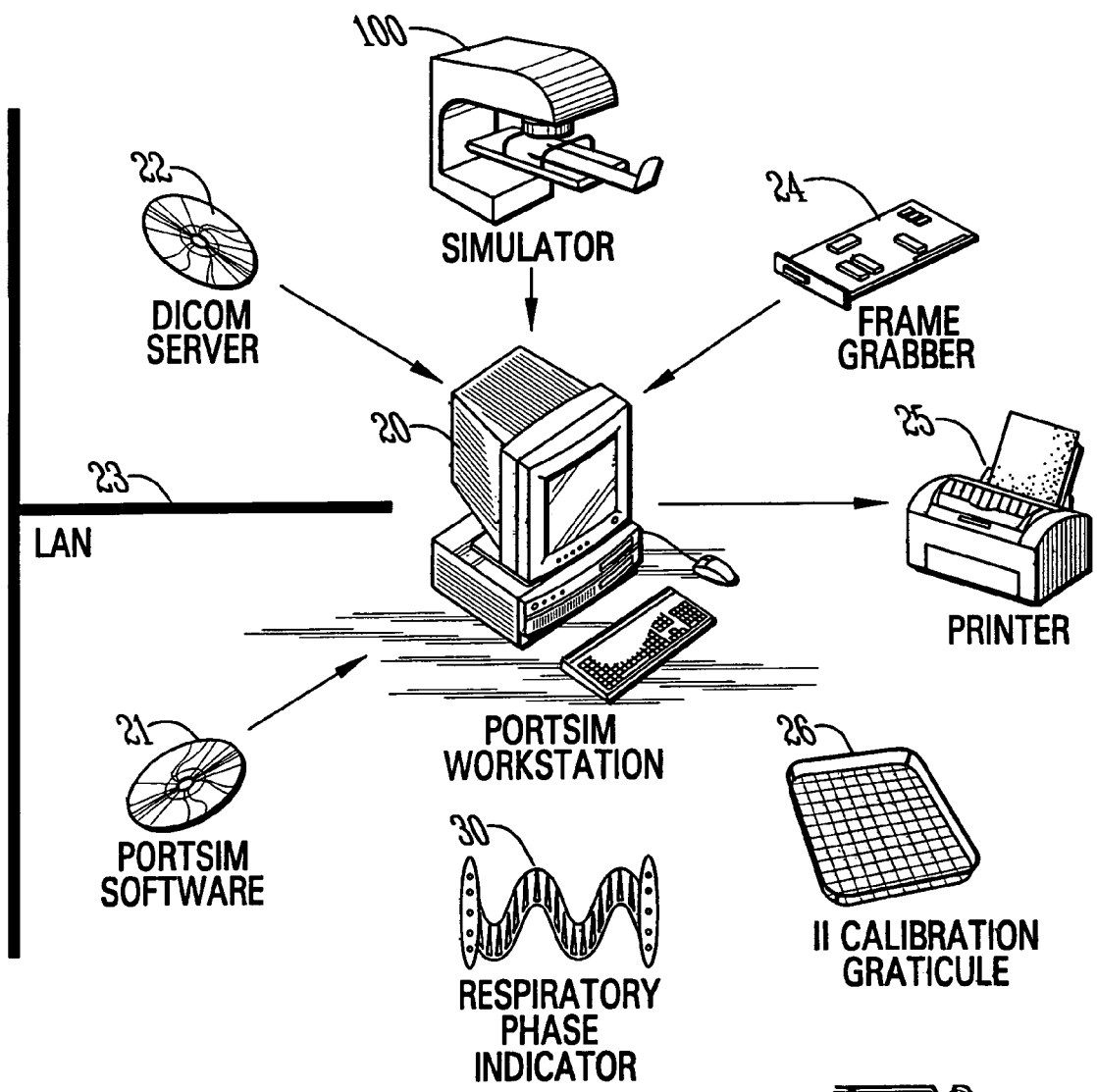
FIG. 8 is a diagram illustrating the components of the system of the present invention.
Figure 9:
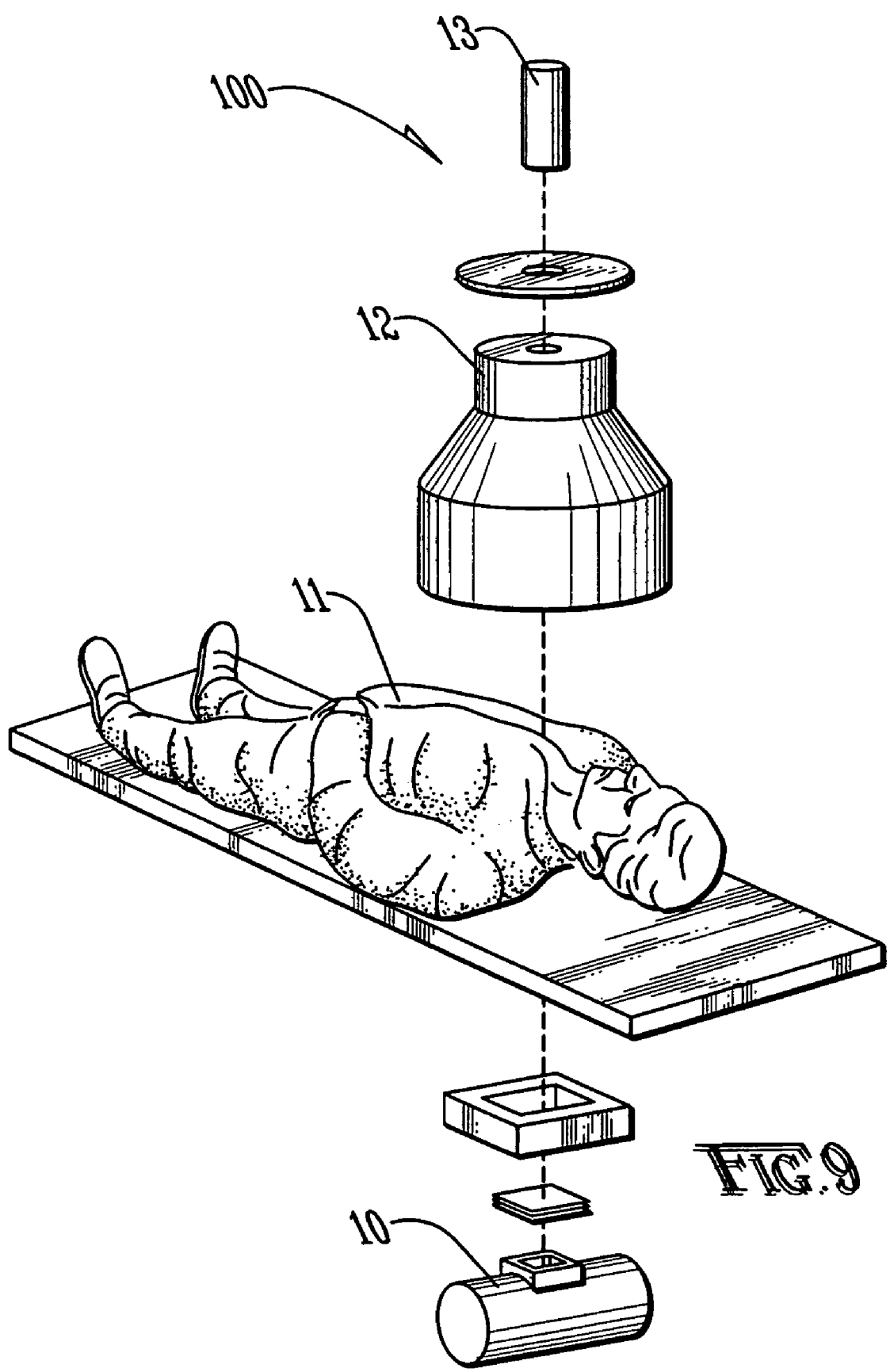
FIG. 9 is a diagram illustrating the elements of a conventional simulator with an image intensifier.

The software of the present invention interfaces with a conventional simulator 100 operating in the fluoroscopic mode. A frame grabber is used to obtain live images from the image intensifier (II). The patient's treatment plan, including DRR's, beams, contours and MLCs can be imported into the system. Distortion corrected fluoroscopic images can be compared against the DDRs to verify beam and isocenter placement. Both static and dynamic MLCs can be superimposed on the fluoroscopic images to verify beam aperture prior to treatment. Volume contours can also be projected to verify target position and coverage. Patient setup and targeting uncertainty can be quantified at the time of the simulation. The complete simulation process can be recorded for later review and analysis. A traditional fluoroscopic simulator 100 is shown in FIG. 9. The x-ray tube 10 generates x-rays that pass through the body of the patient 11 and are received by the fluoroscope and image intensifier (II) 12. The image formed on the fluoroscope and image intensifier 12 is captured by the video camera 13. A frame grabber 24 (shown in FIG. 8) captures sequential fluoroscopic images for processing by the software of the present invention.

In order for the present invention to carry out dynamic simulations, it is necessary that the system have the following capabilities:

1. Pin-cushion distortion and S-distortion of the image intensifier 12 have to be corrected in real-time. The term "real-time" is intended to refer to the performance of all processing operations at such a speed that the output video frame rate is equal to the simulator video frame rate.

2. The patient's respiration phase has to be detected within one frame interval without compromising the image acquisition rate.

3. Various overlays (reference image, contours, jaws, MLC and the like) have to be rendered in real-time.

4. The simulation process should be recorded at high frame rate (>15 frames/second) in high quality images.

The present invention as shown in overview in FIG. 8 comprises a computer system 20 hosting the software 21 described hereinafter and interfaced with various data processing systems, such as a DICOM server 22, LAN 23 and other systems as desired, such as a printer 25. The computer system 20 also receives video inputs from a video camera 13 in a conventional simulator shown in FIG. 9. The respiratory phase indicator 30 as described below is used to imprint a phase signal onto the fluoroscopic image from which the phase information is extracted by the software. Images are displayed on a monitor 94. A calibration graticule 26 is used in conjunction with the distortion correction of the image intensifier 12 as described below.

Figure 1:
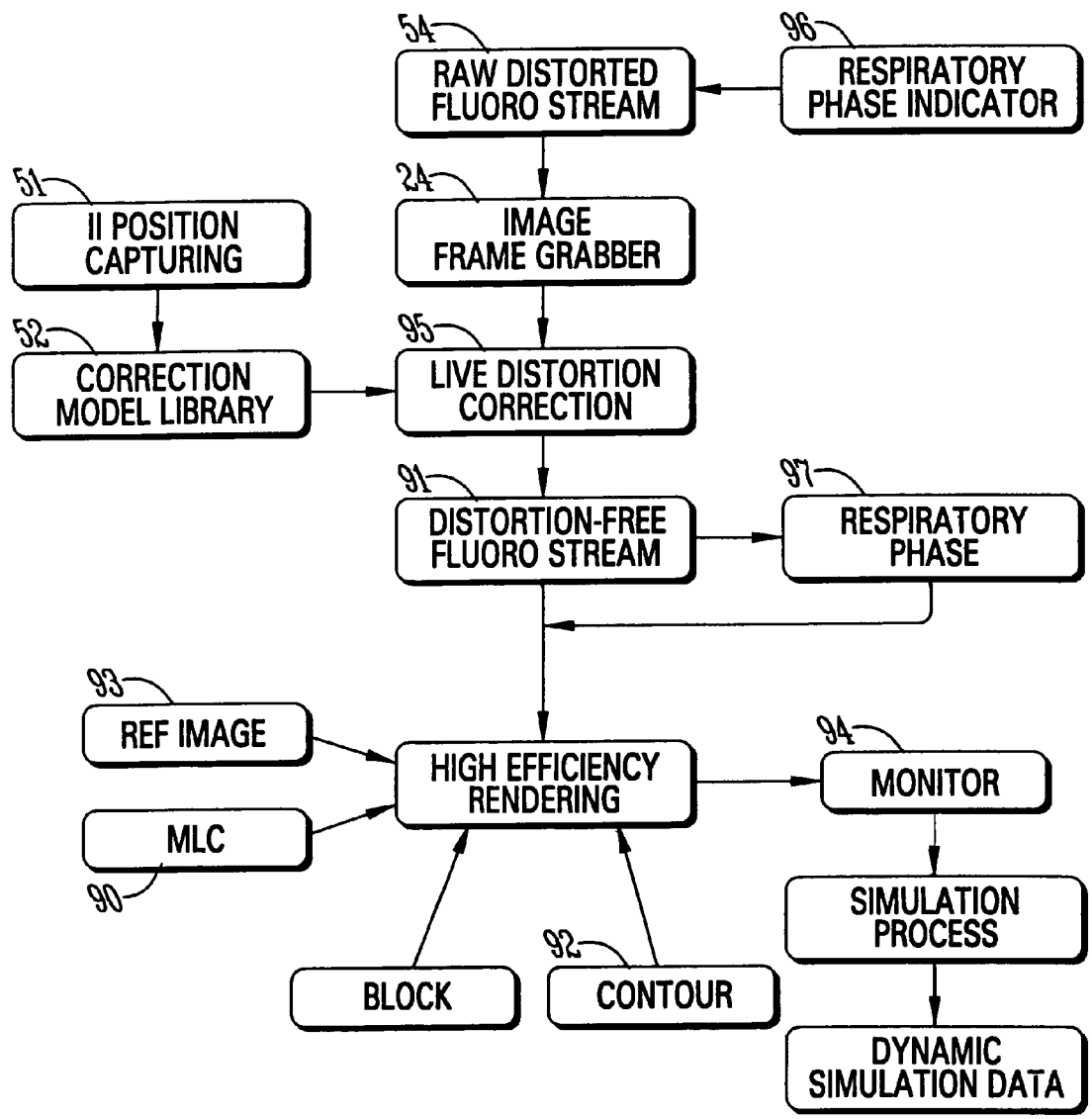
FIG. 1 is a block diagram of the real-time distortion correction method of the present invention along with respiratory phase detection.

With reference to FIG. 1, the present invention not only performs a virtual superposition of static MLC fields 90 on distortion free fluoroscopic images 91, but also allows for dynamic segment display for IMRT fields and projection of anatomic contours 92 imported from other modalities. Additionally, registration tools allow for co-registration and correlation analysis of the fluoroscopic images against the digitally reconstructed radiographs (DRR's) obtained from a treatment planning station.

The system utilizes as much of the available information as possible to verify patient setup and field placement. Data sources include the fluoroscopic images captured from the image intensifier 12 using by the frame grabber 24; the reference image set 93, including orthogonal DRR images and portal films or portal images of previous treatments; anatomical geometry information, which can be retrieved from a virtual simulation workstation or treatment planning system; and treatment field information, including gantry collimator and couch angle, SSD, block shape or MLC control information, which can be imported from a treatment planning system.

Figure 3:
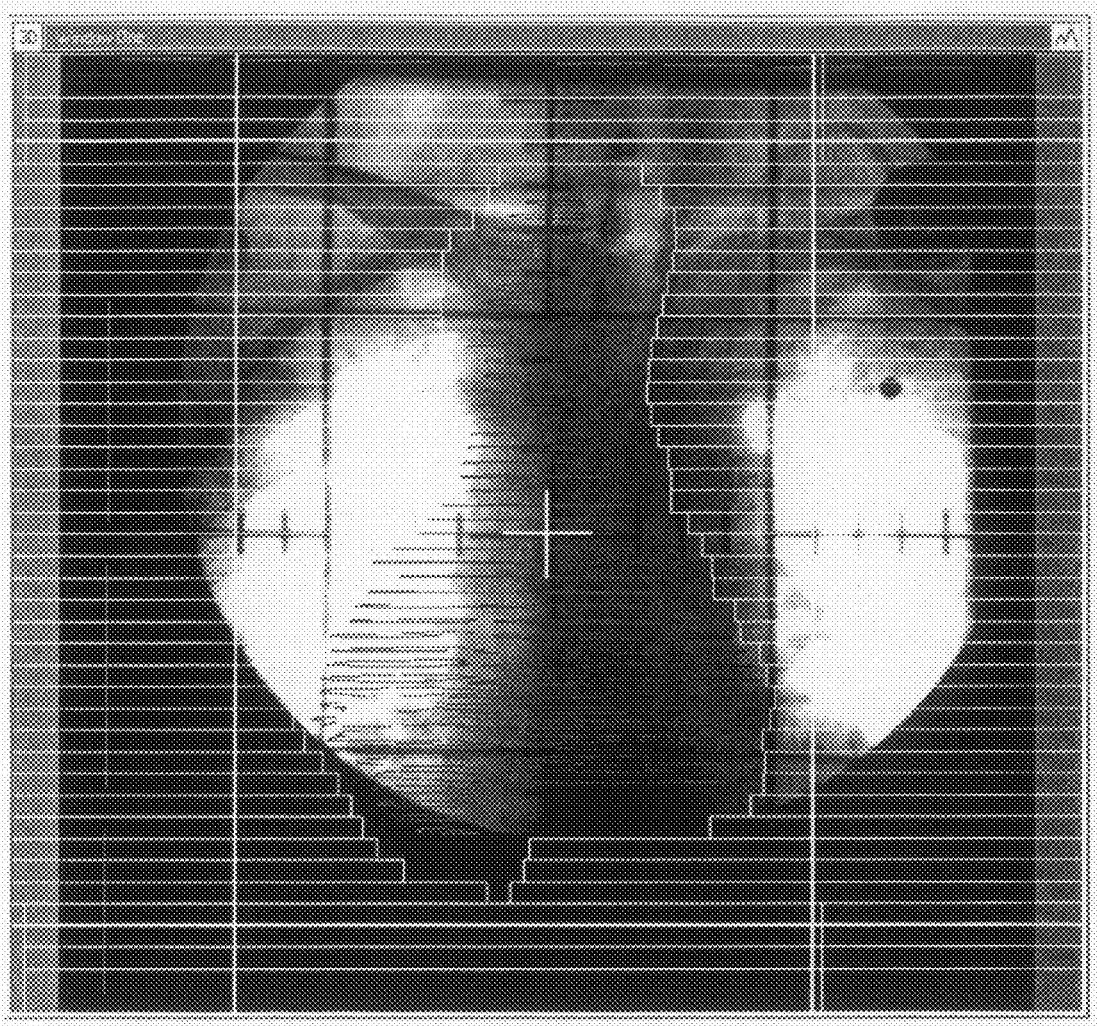
FIG. 3 is a view of an image of static or dynamic MLC and anatomical structures overlying a simulation image.
Figure 4A:
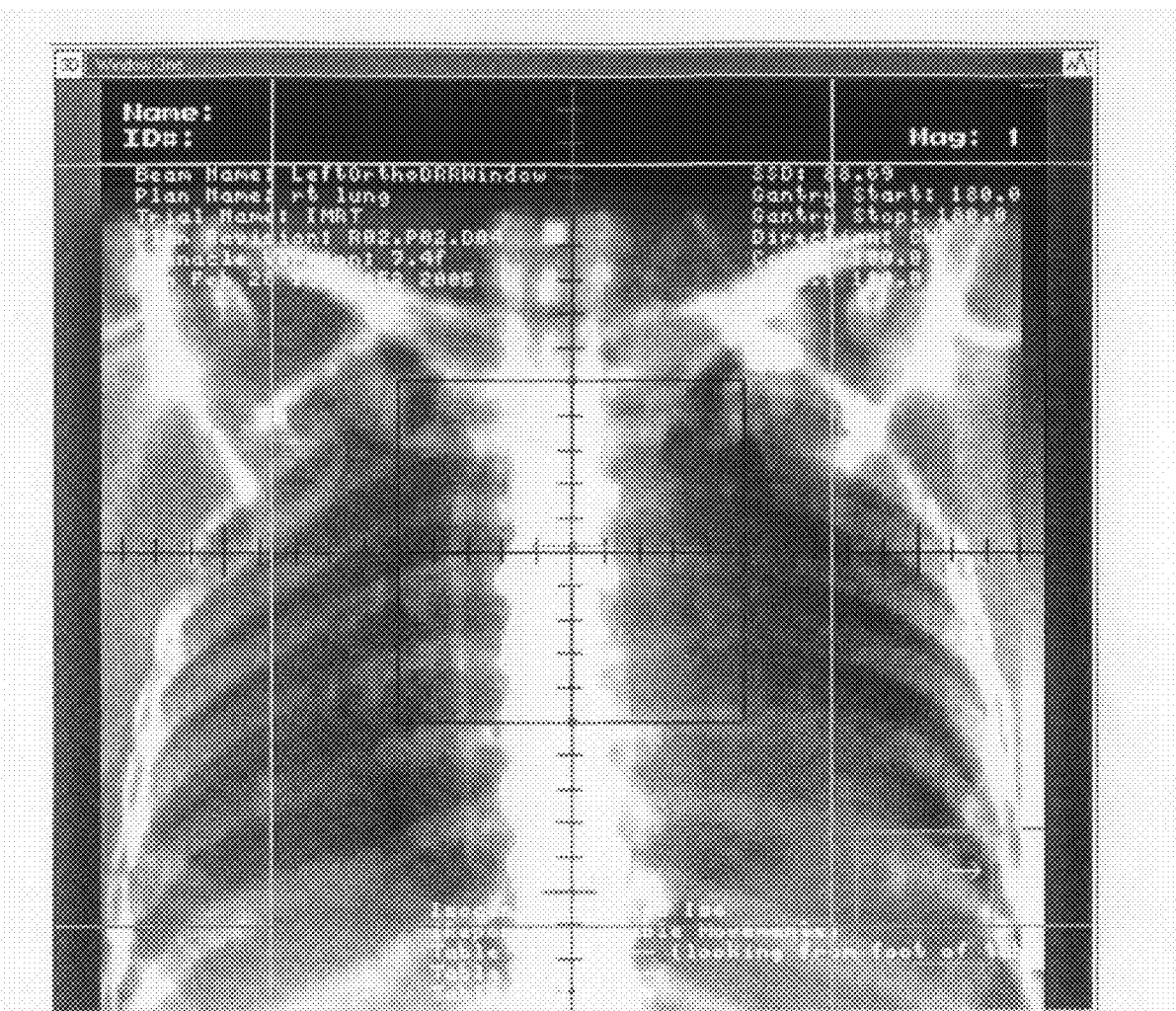
FIGS. 4A and B are views before and after reference image normalization, respectively.
Figure 4B:
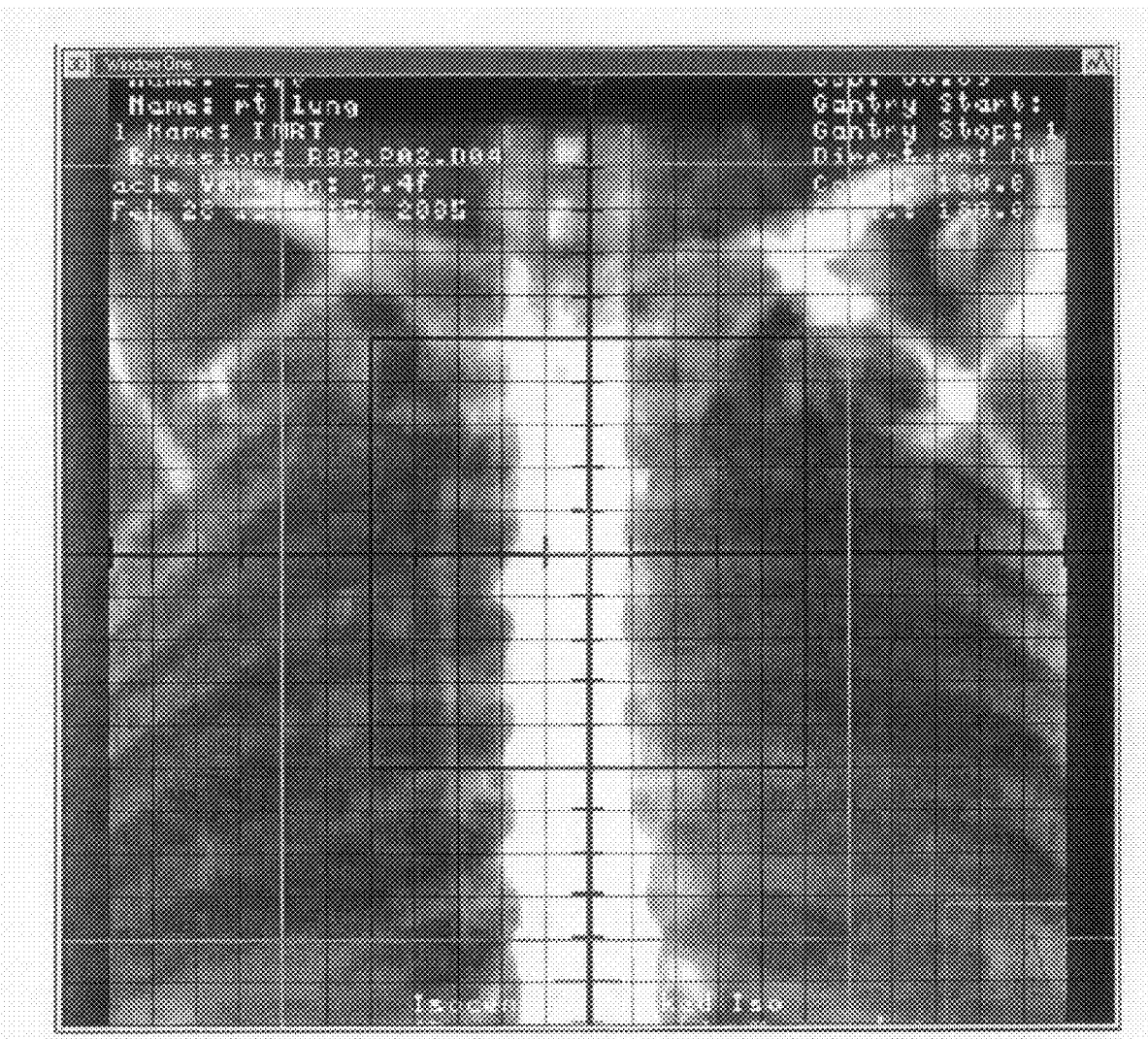
Figure 5A:
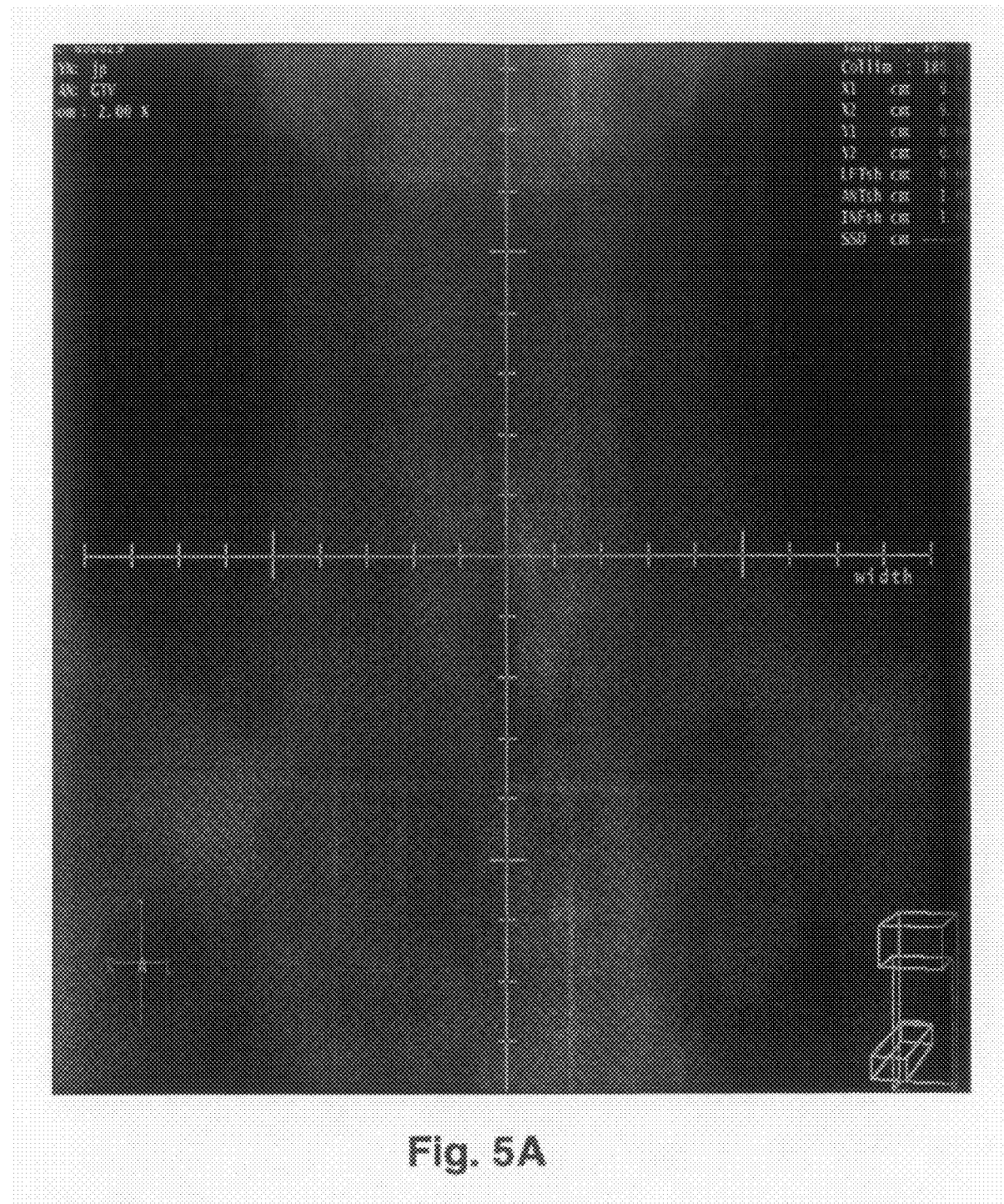
FIG. 5A illustrates fading one image into another.
Figure 5B:
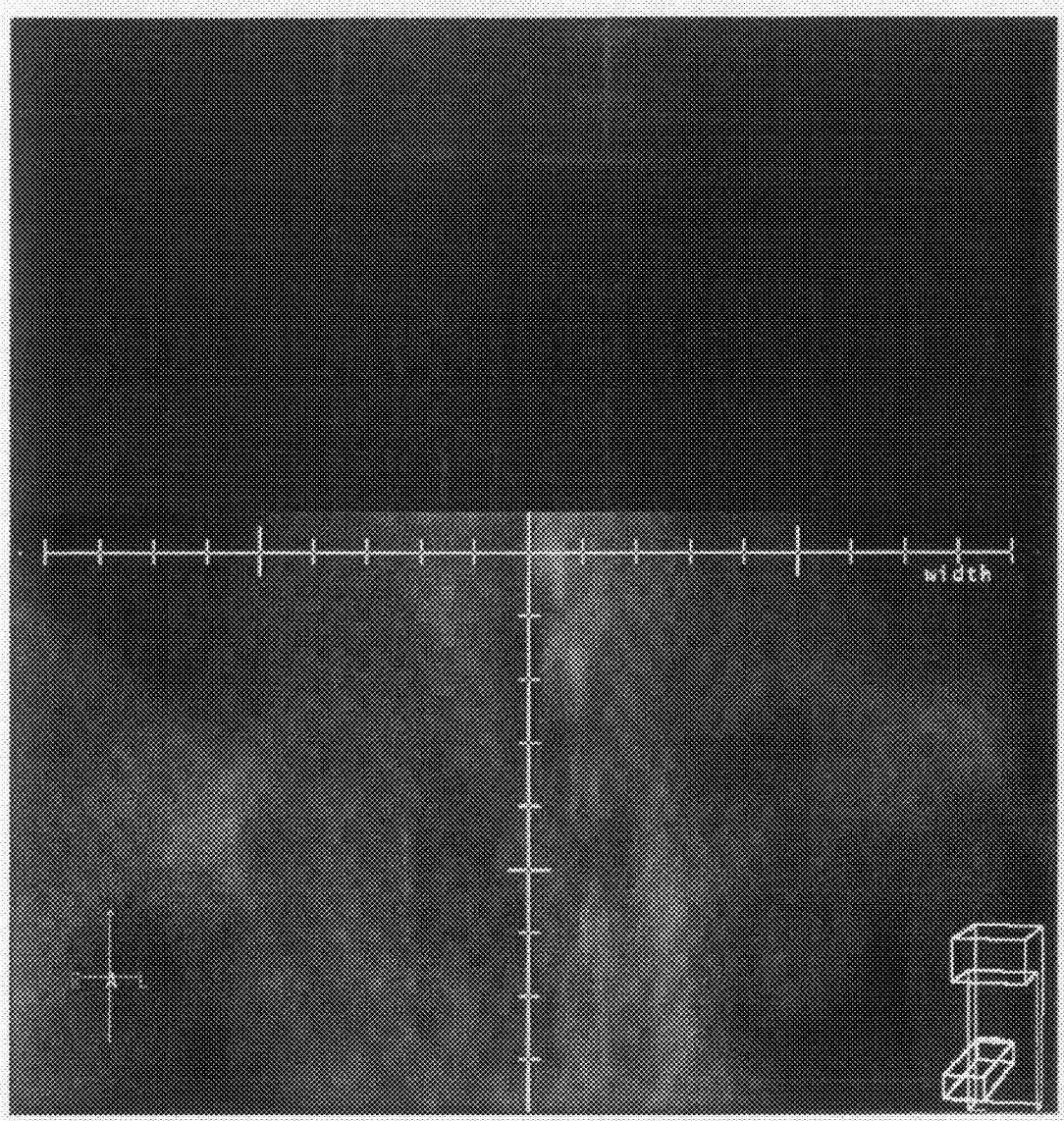
FIG. 5B illustrates horizontal splitting.
Figure 5C:
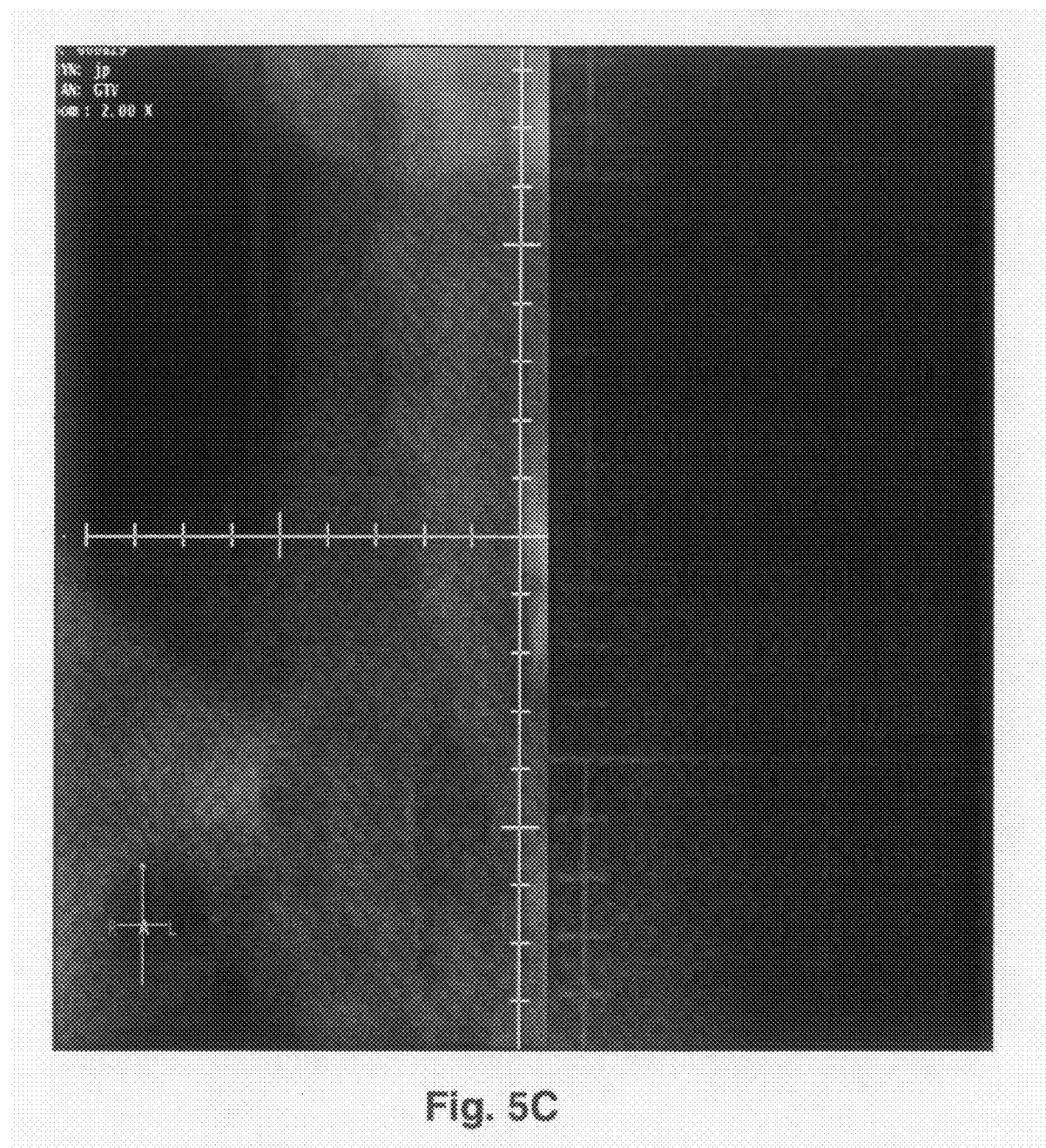
FIG. 5C illustrates vertical splitting.
Figure 5D:
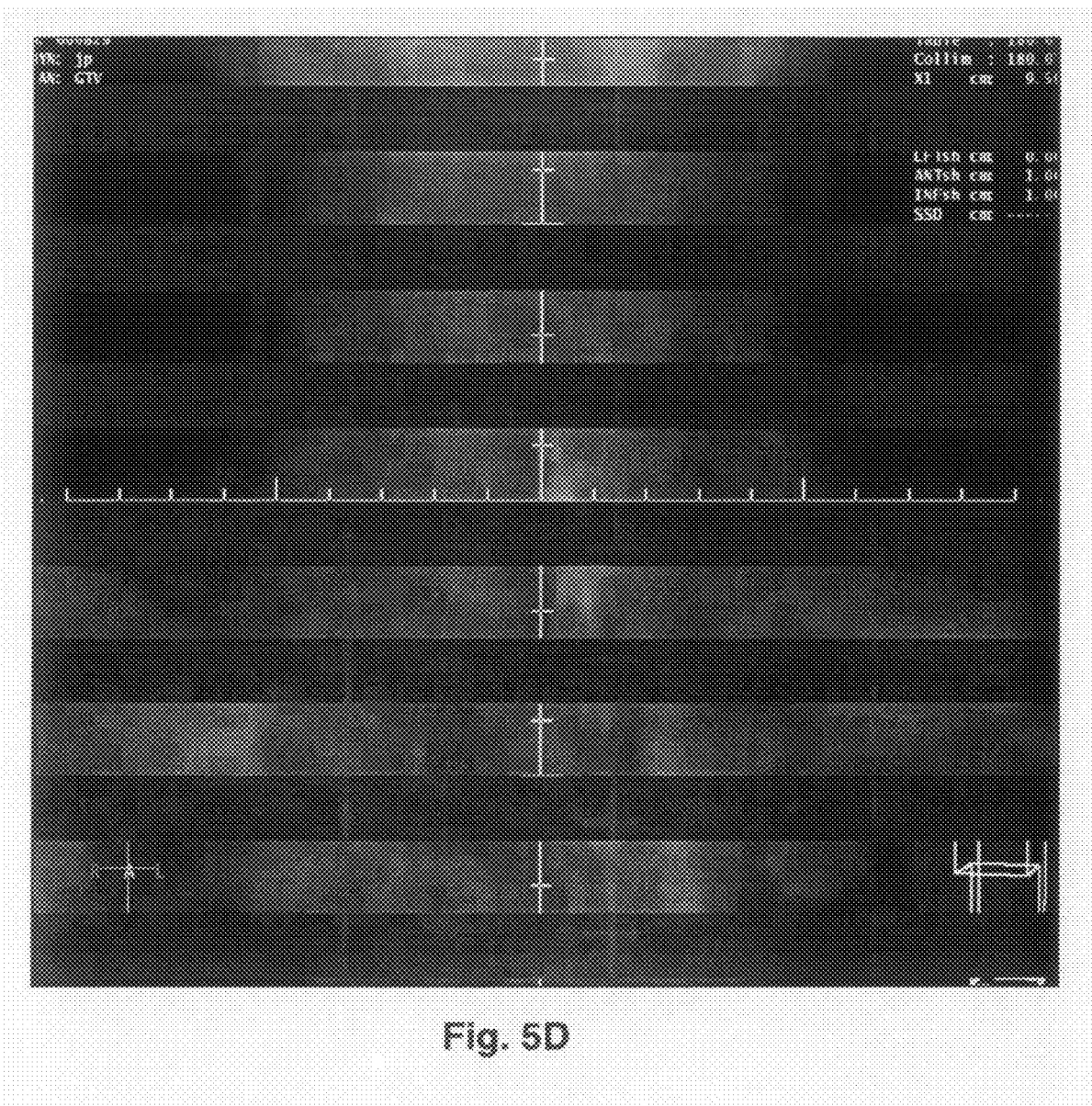
FIG. 5D illustrates a horizontal blind arrangement.
Figure 5E:
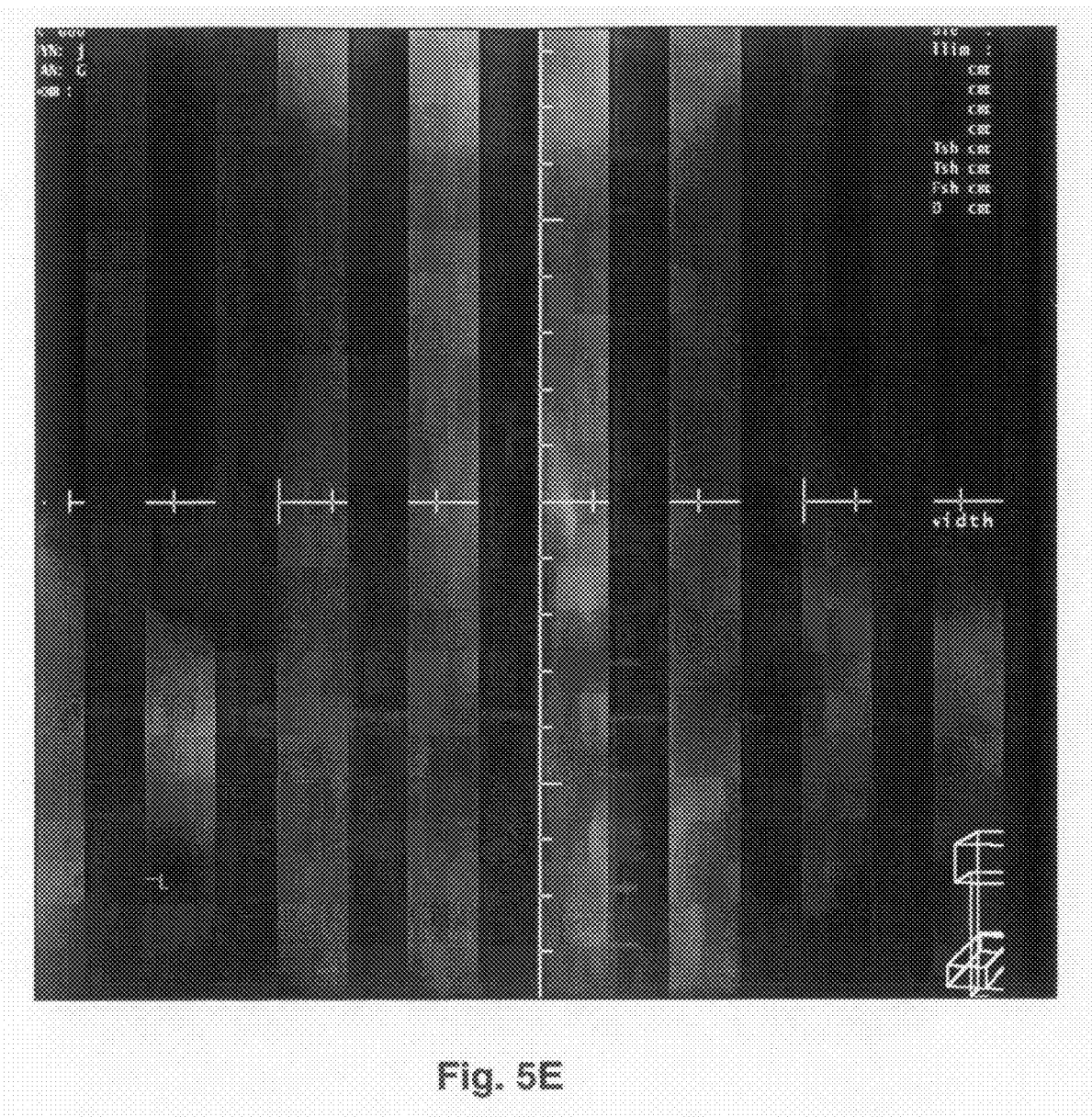
FIG. 5E illustrates a vertical blind arrangement.
Figure 5F:
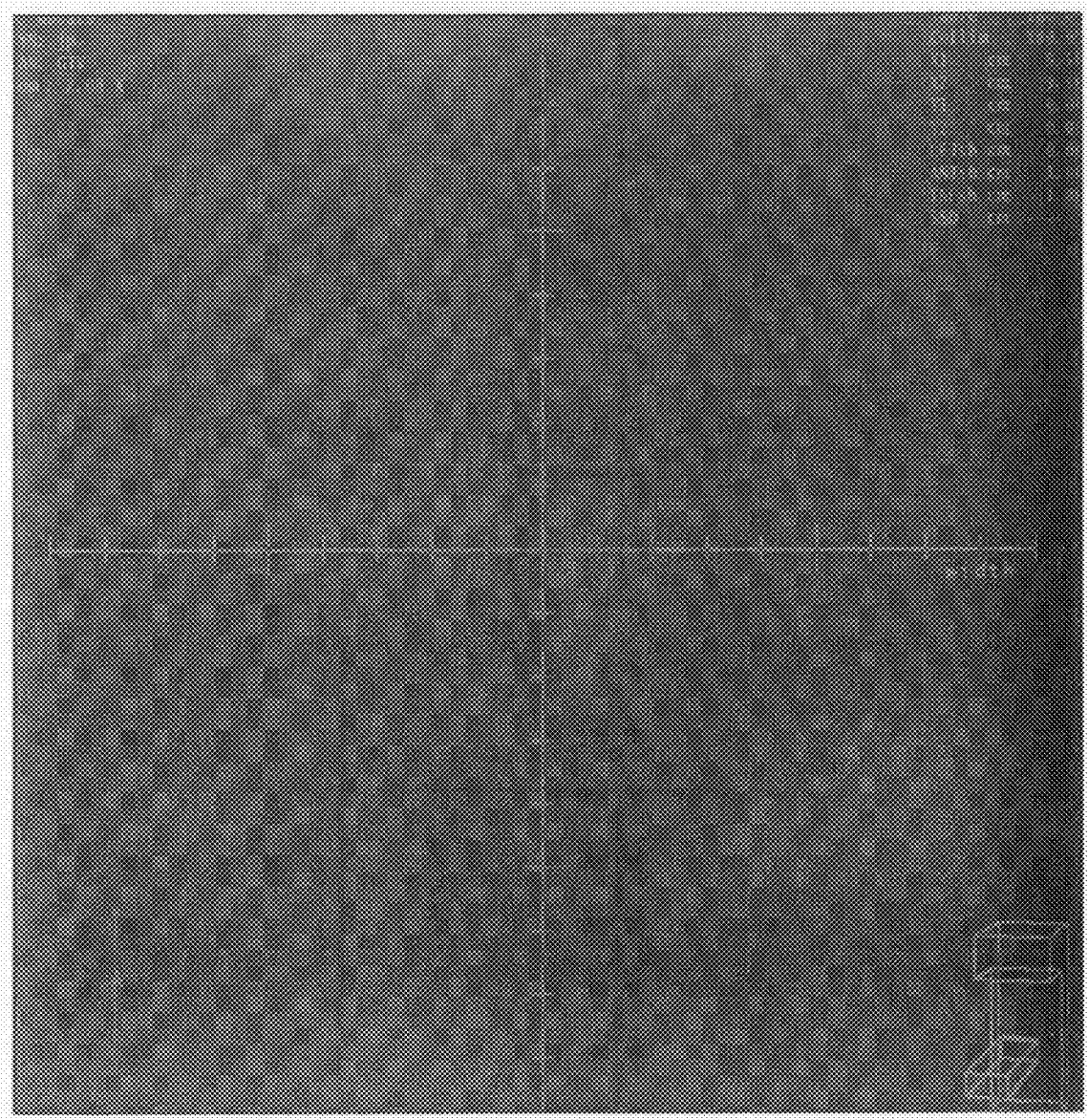
FIG. 5F illustrates subtraction of one image from another.
Figure 6A:
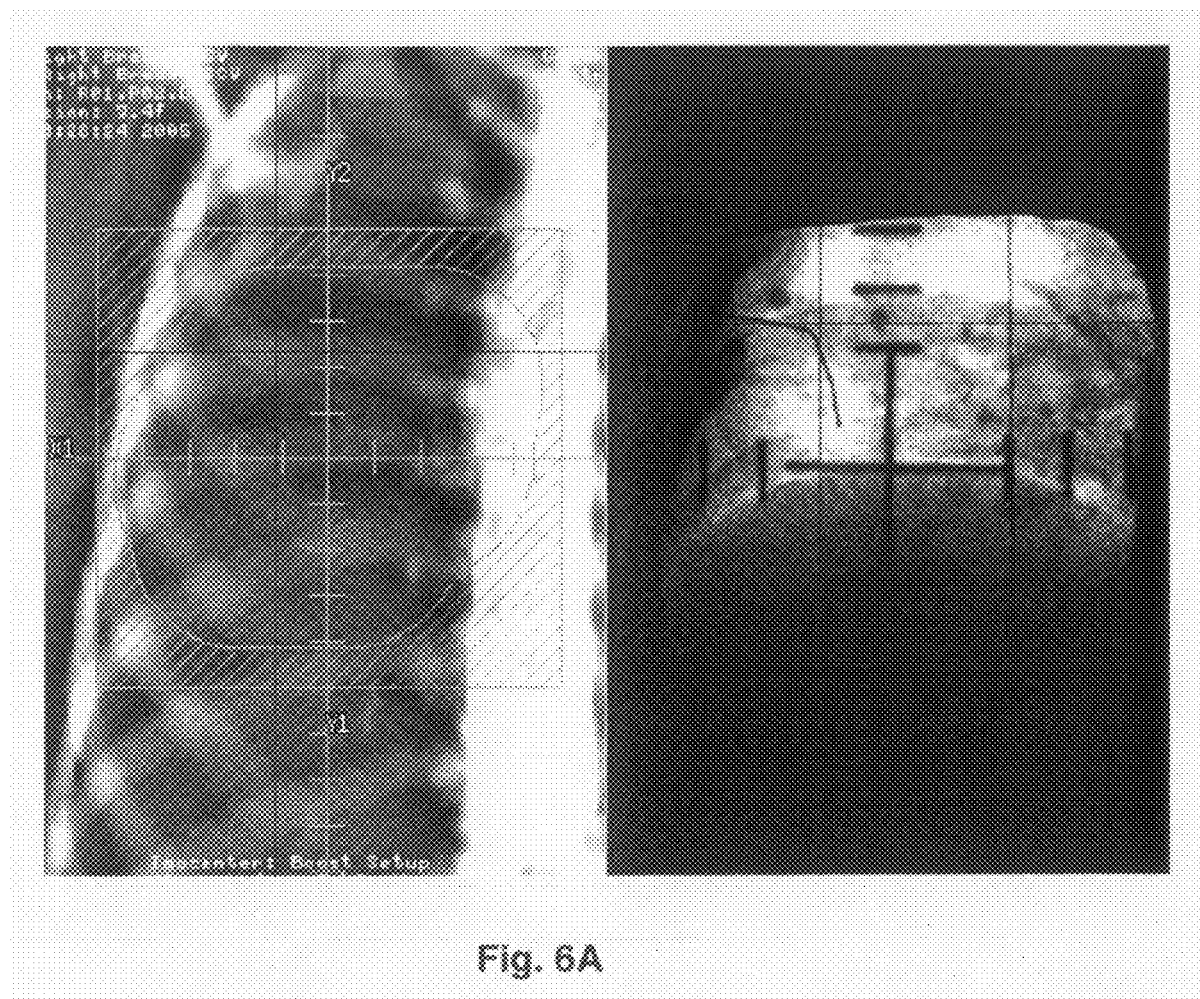
FIG. 6A shows a reference image in the left window and a distortion corrected fluoroscope image in the right window. Overlaid movable crosses in the right window help to accurately locate remote points that are away from the reference frame. The reference image window can be switched off to display the fluoroscopic image in the whole screen.
Figure 6B:
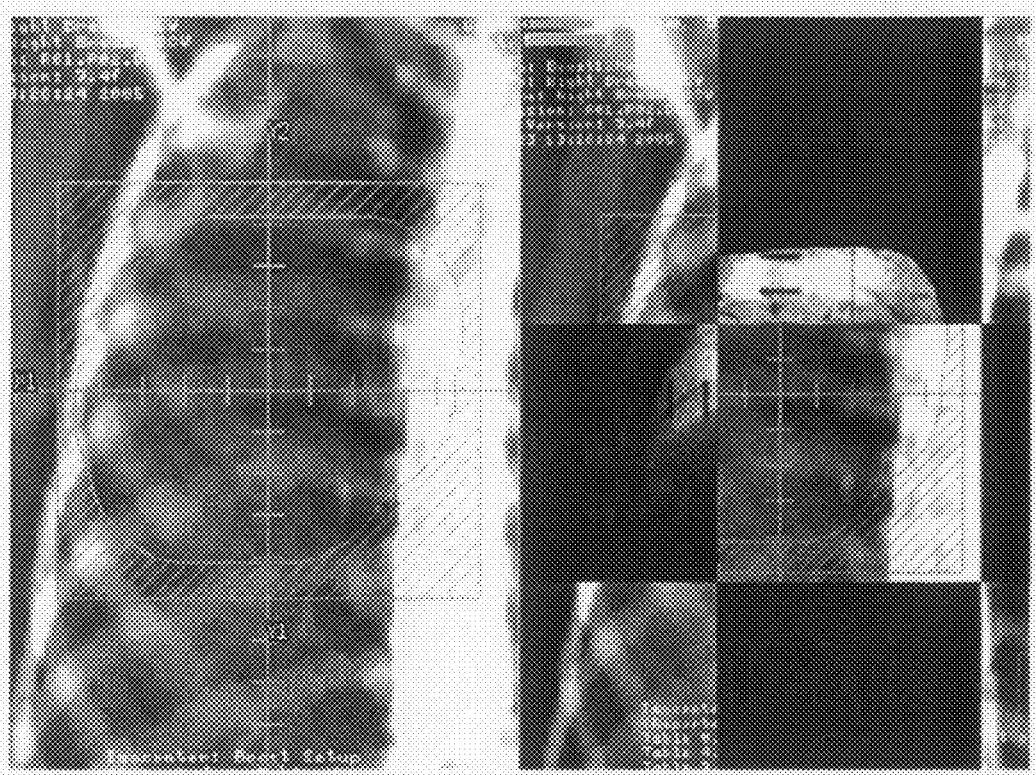
FIG. 6B illustrates a checkerboard pattern.
Figure 6C:
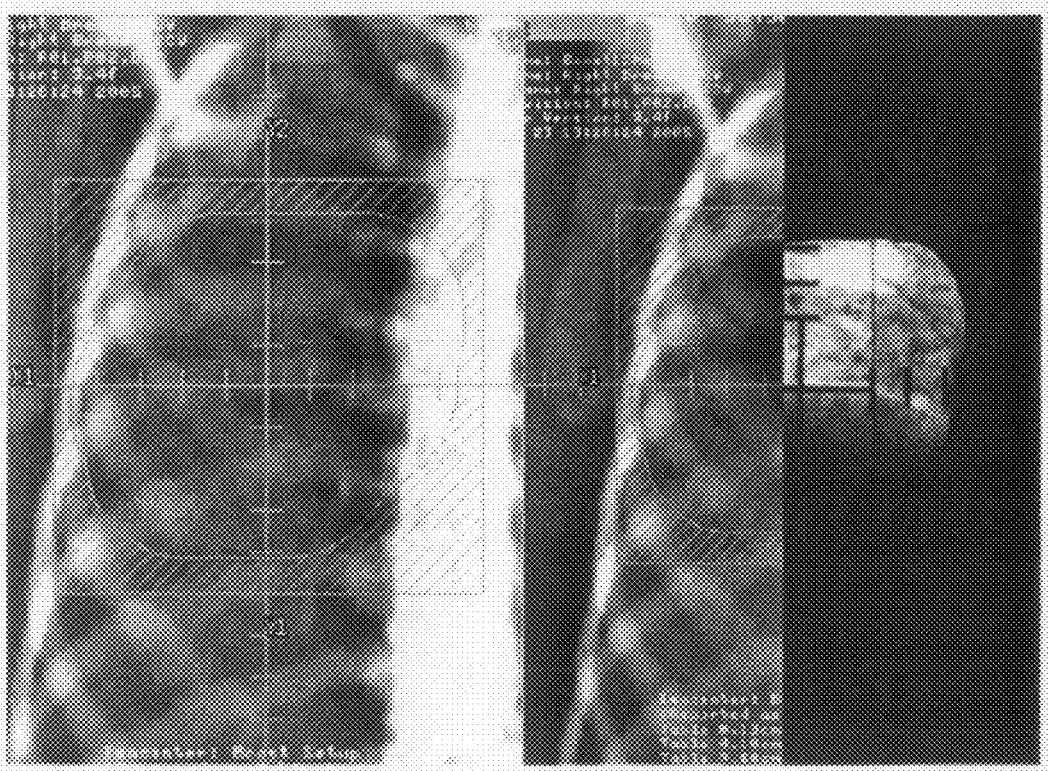
FIGS. 6C, 6D and 6E are similar to the display functions illustrated in FIGS. 5C, 5B and 5A, respectively.
Figure 6D:
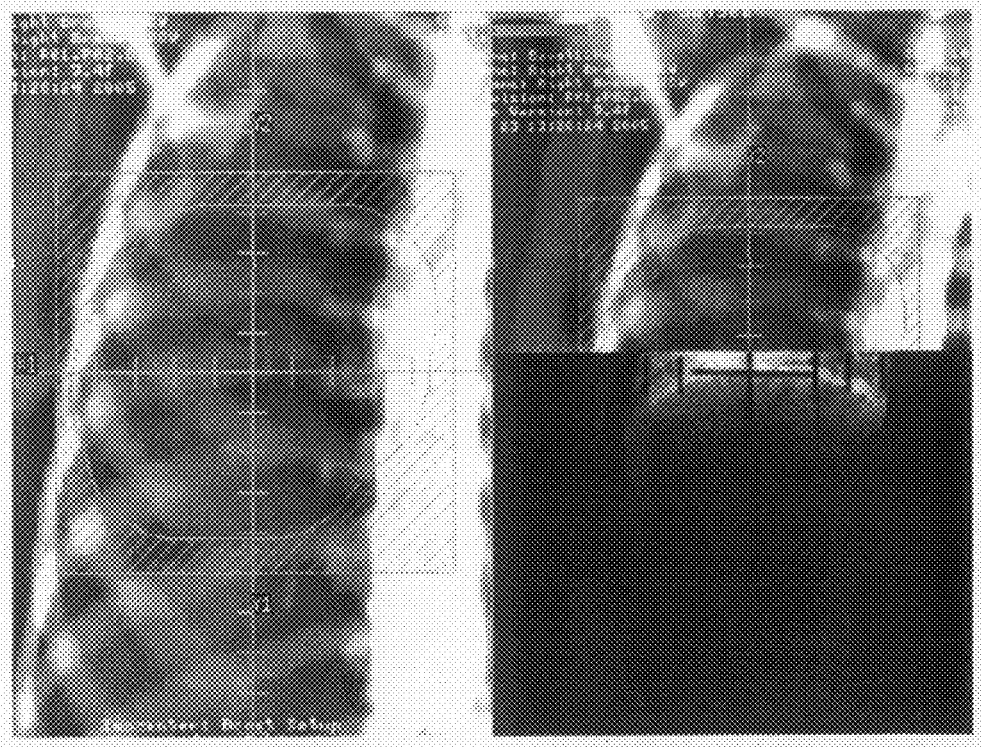
Figure 6E:
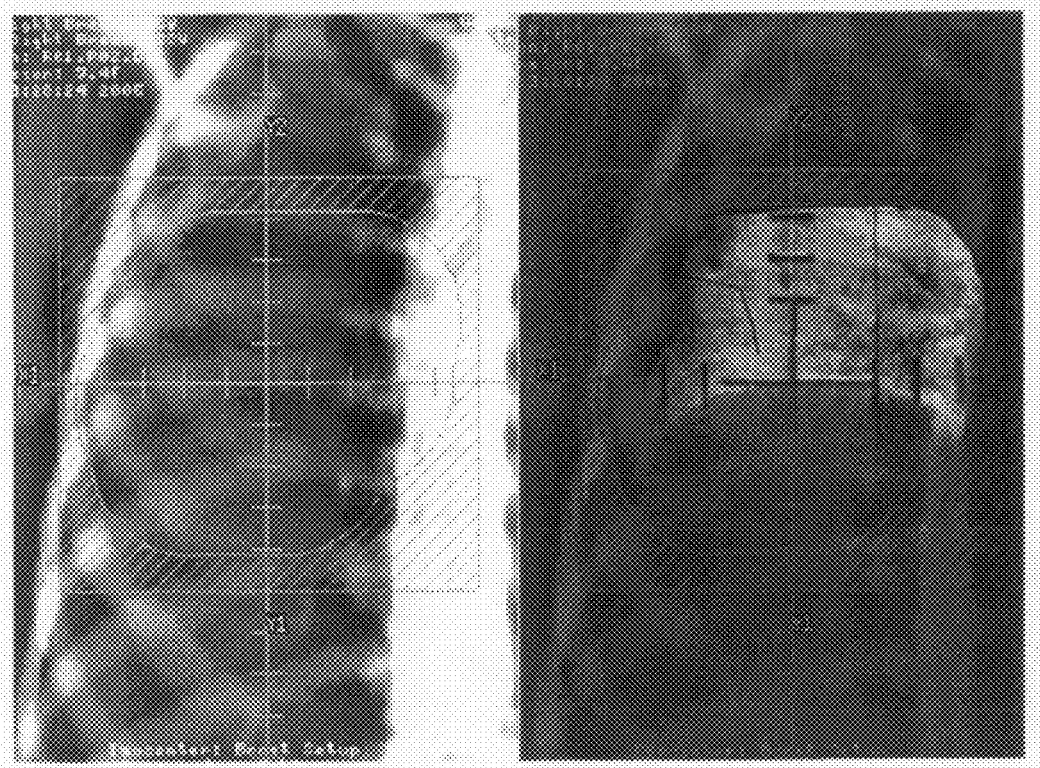
Figure 11:
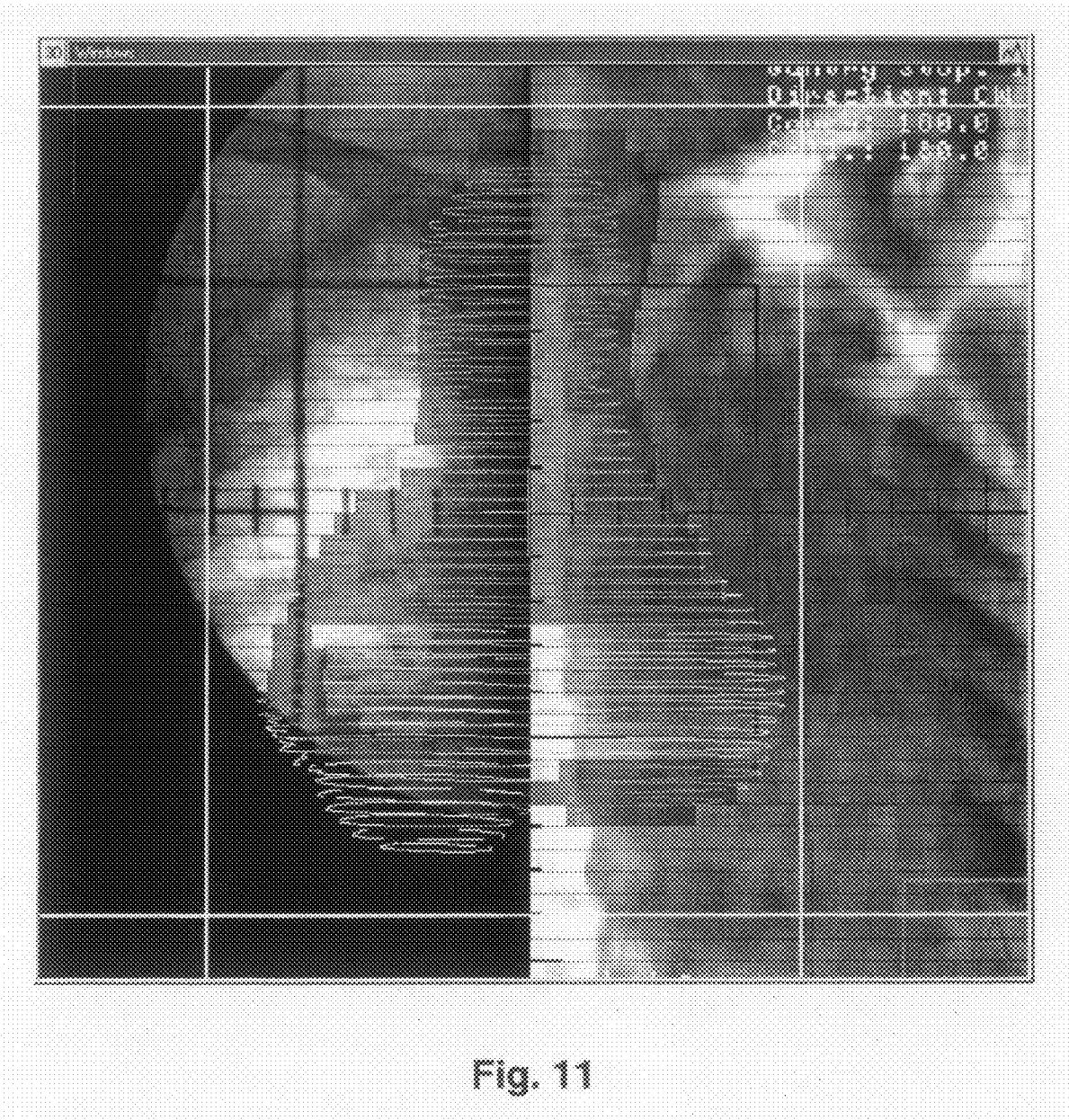
FIG. 11 is a view showing a fluoroscopic image on the left corrected and registered with a DRR on the right in horizontal splitting mode. On top of registered images, contour and dynamic MLC ports are projected.

The primary functions of the system include fluoroscopic image acquisition by a frame grabber 24 that digitizes the live video image at a rate of around 30 frames/second with a desirable image definition of 1024×1024 pixels; graphical overlay of static MLC and block; graphical overlay of dynamic MLC; graphical overlay of anatomic structures; and image registration and fusion as shown in FIGS. 3 and 11. Reference images 93, for example, DRR images, may be registered with fluoroscopic images 91 by pointing out four registration points as shown in FIGS. 4A and B. The images may then be registered according to least-square error criteria. Registered images can be displayed on top of each other in multiple rendering styles in the Monitor Workspace as shown in FIGS. 5A-F. FIG. 5A illustrates fading one image into another. FIG. 5B illustrates horizontal splitting. FIG. 5C illustrates vertical splitting. FIG. 5D illustrates a horizontal blind arrangement. FIG. 5E illustrates a vertical blind arrangement. FIG. 5F illustrates subtraction of one image from another.

FIG. 6 represents a series of online image comparison rendering styles in the Monitor Workspace (full screen mode) while simulating the patient. FIG. 6A shows a reference image in the left window and a distortion corrected fluoroscope image in the right window. Overlaid movable crosses in the right window help to accurately locate remote points that are away from the reference frame. The reference image window can be switched off to display the fluoroscopic image in the whole screen. FIGS. 6C, 6D and 6E are similar to the display functions illustrated in FIGS. 5C, 5B and 5A, respectively. FIG. 6B illustrates a checkerboard pattern.

Figure 7:
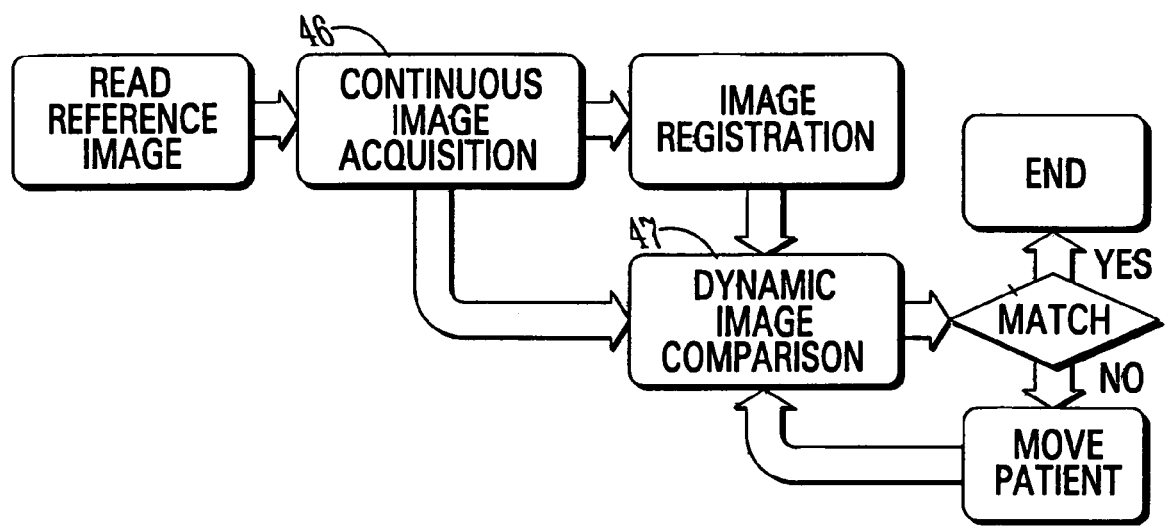
FIG. 7 is a diagram of a masked image acquisition technique.

Masked Image Acquisition allows for dynamic comparison between the reference image and the fluoroscopic image. Masked Image Acquisition is represented in FIG. 7. It is a real-time image comparison technique and requires a frame grabber 24 of high performance with the following features: (i) 8-bit overlay; and (ii) masked image acquisition. The fluoroscopic images 46 are acquired continuously and the comparison is dynamic 47.

The reference image can be moved around in the display manually to get a good match with the fluoroscopic image by using the display styles shown in FIGS. 5A-F.

As options, the simulation image with graphic overlay drawing with patient-specific information can be printed out on printer 25 or saved into an image file as a medical record, or a movie of the treatment simulation can be generated, for example in standard AVI format. A movie format in which all treatment parameters such as MLC segments, block geometry, reference images, anatomic structure and the like are stored together with image sequences is desirable for data processing and analysis for quality assurance procedures. It is also desirable for the later movie format to be convertible into the AVI format.

Figure 2:
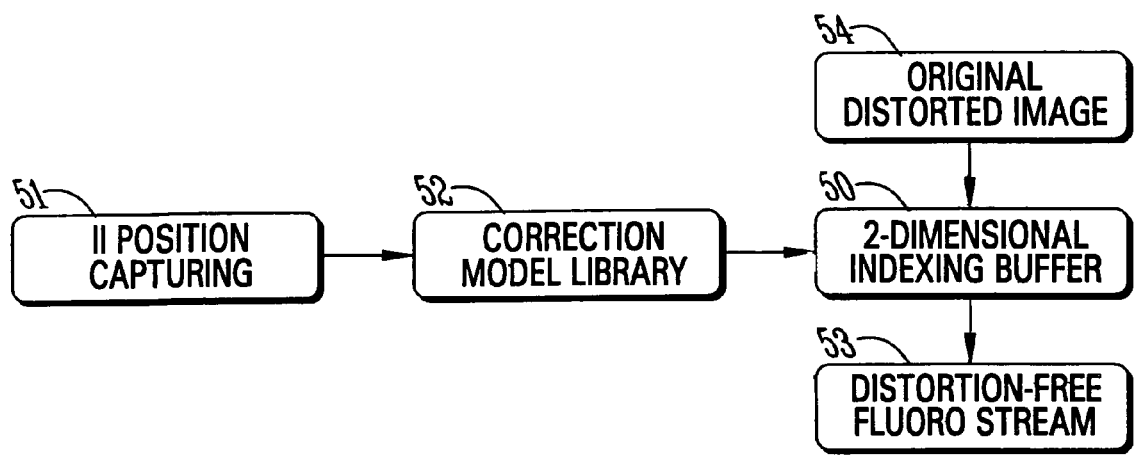
FIG. 2 is block diagram of the real-time image distortion correction method of the present invention.

Image distortion correction is a mandatory step toward direct image fusion. To achieve on-line real-time simulation under the guidance of reference images and other overlay displays, the spatial distortion of the image intensifier 12, both pin-cushion distortion and S-distortion, has to be corrected in real-time without compromising the efficiency of realistic MLC simulation and simulation process recording. A frame rate of simulation at 30 frames per second at a resolution of 1024×1024 pixels is desirable. A recording frame rate of either 30 frames per second or 15 frames per second is also desirable. FIGS. 1 and 2 illustrate the principle components of on-line simulation as practiced in the present invention.

II image distortion varies with gantry angle and II position (lateral, longitudinal and vertical). Conventional fluoroscopy during simulation often involves the arbitrary panning and scrolling of the image intensifier 12 under the control or supervision of the oncologist, and it will not always be possible to use a standard gantry angle for many oblique fields, particularly where IMRT planning is employed. In order to obtain a distortion corrected image, we ideally and theoretically have to apply a correction model on the II 12 at all possible positions, which is impractical.

Figure 10A:
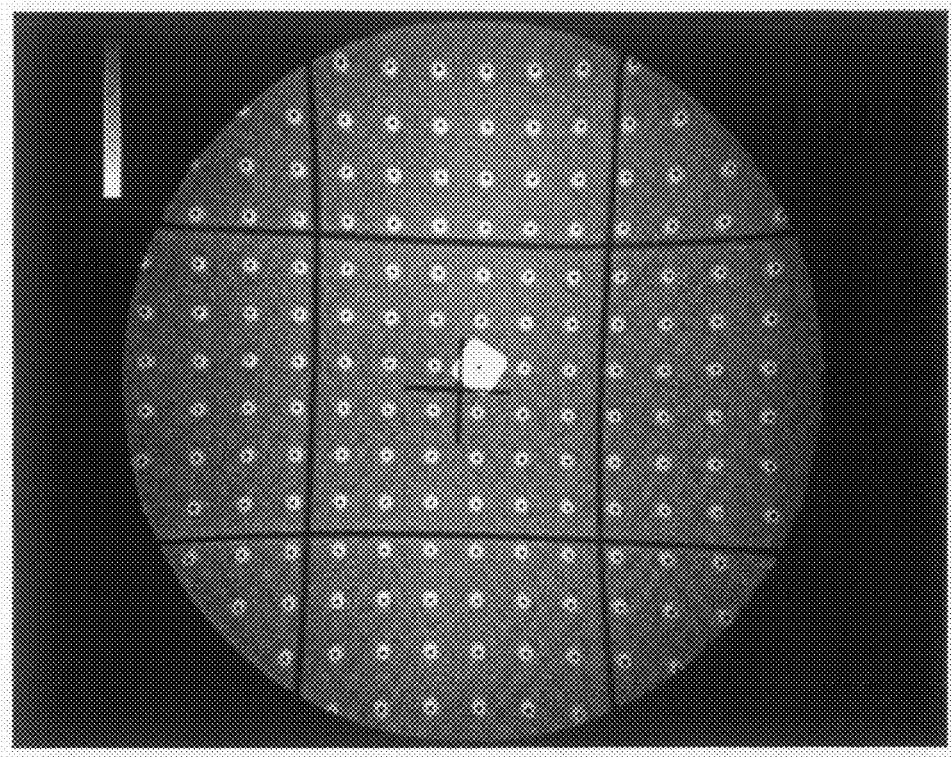
FIG. 10A is a view of an uncorrected image from the image intensifier with a Varian® calibration graticule in place.
Figure 10B:
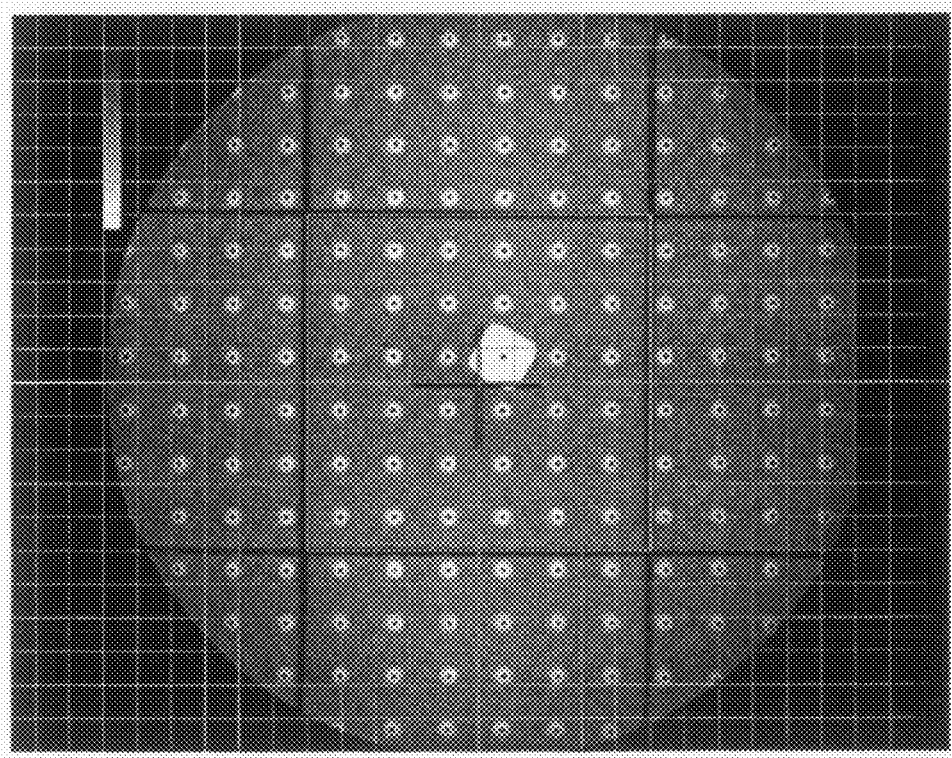
FIG. 10B shows the distortion corrected image of FIG. 10A.

To achieve real-time image distortion correction 95, a calibration graticule 26 is used to build calibration models at pre-selected II 12 positions. FIG. 10A presents an uncorrected image with a Varian® calibration graticule 26 in place and FIG. 10B shows a distortion-corrected image with artificial grid displayed. Model interpolation is utilized for arbitrary positions of the II 12. By using this programming technique as described more fully below, distortion correction is achieved in real-time.

The approach of the present invention is to build a number of models, one hundred and twenty in the preferred embodiment, based on an even distribution of image intensifier 12 positions in space. The specific correct model for any position in space is obtained by interpolation among models of neighboring points. The interpolated model provides the correction model for any point in space. Then the interpolated correction model is applied to the distorted image to obtain the corrected distortion-free image. Since the application of a correction model to all images cannot be done in real-time due to the computationally-intensive nature of the calculations, the present invention uses a unique method to achieve real-time image correction as shown in FIG. 2. The first step 51 is capturing the position of the image intensifier 12. The corresponding correction model is interpolated from a library 52 of correction models developed as described above for the basic one hundred and twenty image intensifier 12 positions. Next, a two-dimensional indexing buffer 50 is created from the corresponding interpolated correction model since memory indexing is much faster than formula calculation. The indexing buffer 50 has the same size as the corrected image. Each pixel on the corrected image will have a corresponding indexing address in the corresponding cell of the indexing buffer 50, which in turn corresponds to a sampling address of a pixel in original distorted image. The indexing buffer 50, generated from the interpolated correction model, is used to rapidly create the stream of corrected images 53 from the original distorted images 54 in real-time as shown in FIG. 2.

To summarize the procedure: (1) look to the buffer 50 for a point in the corrected image, (2) from the buffer 50 obtain index information that points to a particular location in the uncorrected image, and (3) assign the data for that point in the uncorrected image to the point in the corrected image. Repeat the process to build up the corrected image.

The fluoroscopic video signal from the image intensifier 12 is input to the image frame grabber 24 at a rate of 30 frames per second. The image resolution in the preferred embodiment is 1024×1024 pixels. Fusing reference DRR's with real-time fluoroscopic images in different patterns as shown in FIGS. 5A-F and 6A-E is very helpful in image comparison.

The present invention is capable of dynamic treatment simulation for respiratory-gated intensity-modulated radiation therapy (RGIMRT).

Figure 13:
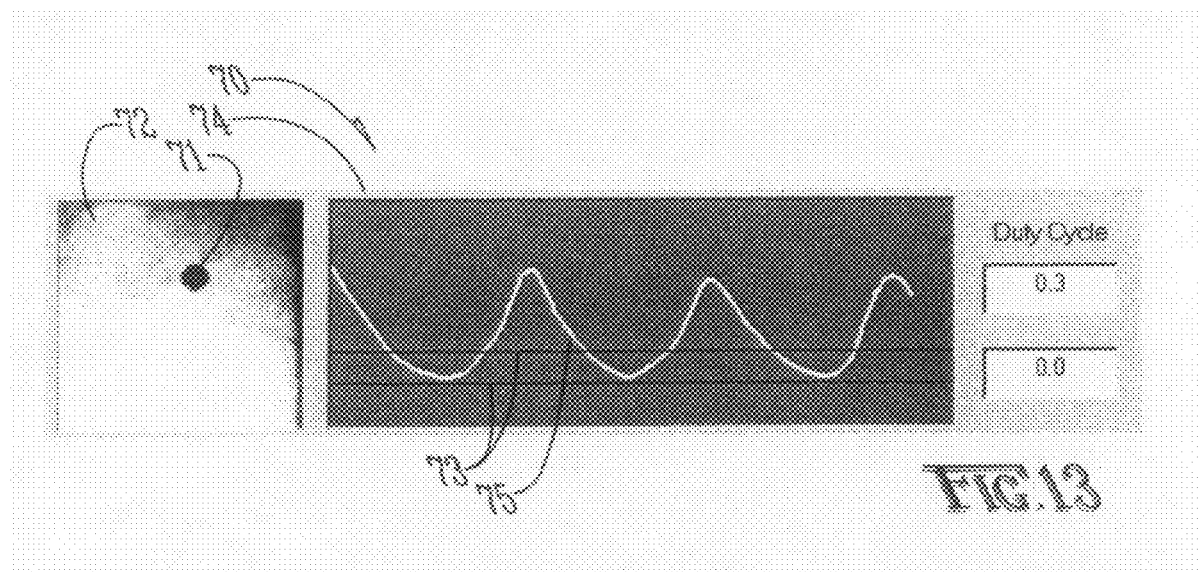
FIG. 13 is a view of the respiration phase detection control panel. The black dot in the left window represents the respiration phase marker on the fluoroscopic image. The straight lines in the middle window define the duty cycle thresholds. The curved line is the respiration cycle signal.

Prior to simulation, a set of DRR's at different respiration phases along with the corresponding anatomic contours are imported from the treatment planning station. The respiratory rhythm and cycle of the patient is captured using a respiratory phase indicator 96 including a radio-opaque marker 60 which reflects the circumference change of a binding belt 61 around the patient's chest 62. The marker 60 correlates with the respiratory cycle and can be easily detected. A typical display of the respiration phase control panel 70 is shown in FIG. 13. The black dot 71 in the left window 72 represents the respiratory phase marker 60 on the fluoroscopic image. The straight lines 73 in the middle window 74 define the duty cycle thresholds. The curved line 75 is the respiration cycle signal.

Figure 14:
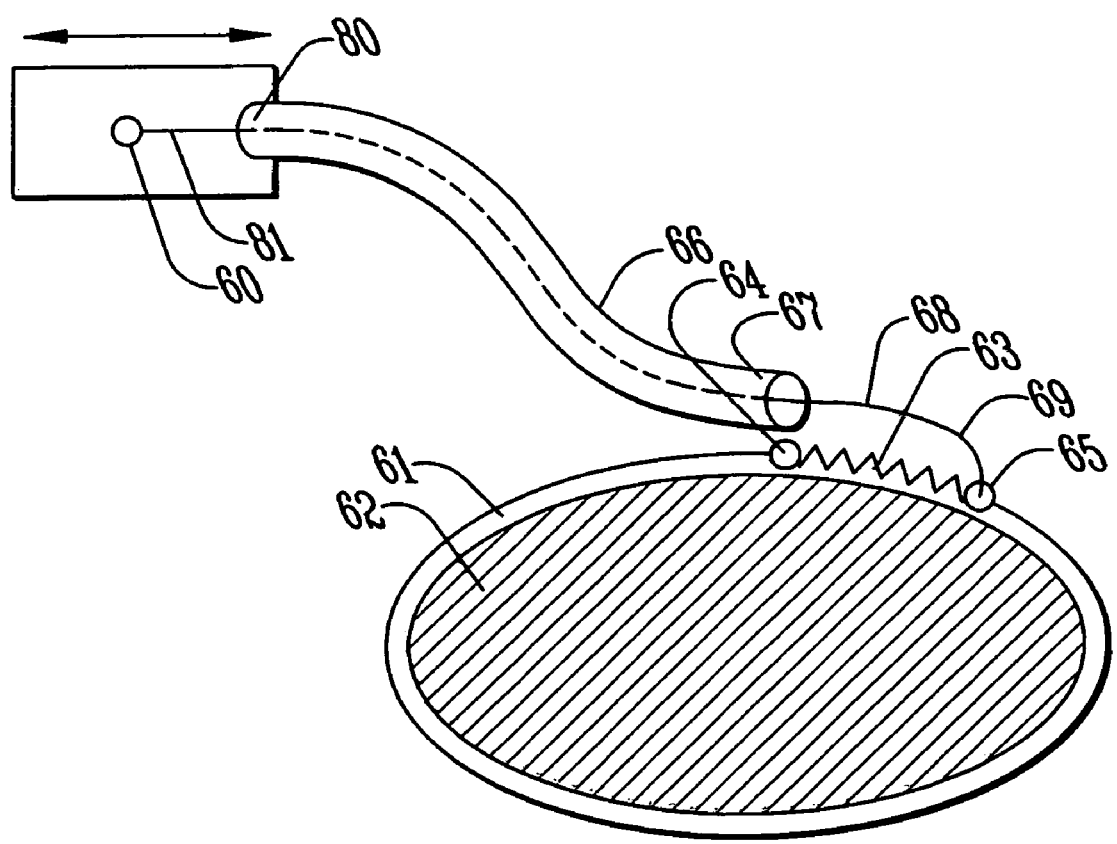
FIG. 14 is an elevation view of the respiration phase indicator of the present invention on the chest of a patient shown in cross-section.

To detect the patient's respiration phase, the radio-opaque marker 60 and driving belt mechanism shown in FIG. 14 detect the circumference change with respiration phase as reflected by the moving marker 60 on the fluoroscopic image of the patient. The marker 60 can be easily detected from the distortion corrected fluoroscopic image stream 91 and thereby the respiratory phase 97. By imprinting the image 71 of the respiration phase marker 60 on the fluoroscopic image, synchronization or mismatch problems are avoided. The circumference change indicator is also more reliable and more sensitive in detecting respiration phase than external markers.

As shown in FIG. 14, the respiratory phase indicator 96 of the present invention uses a belt 61 encircling the chest 62 of the patient to measure changes in the circumference of the chest 62. The changes in the circumference are indicated by linear changes in the position of the radio-opaque marker 60. The belt 61 is provided with an elastic portion 63 extending between a first point 64 and a second point 65 on the belt 61. A tube 66 has a first end 67 in a fixed relationship to the first point 64. A flexible wire 68 having a first end 69 is affixed to the second point 65. The wire 68 passes through the tube 66 and extends beyond a second end 80 of the tube 66. The radio-opaque marker 60 is attached to a second end 81 of the flexible wire 68. Expansion in the circumference of the patient's chest 62 expands the elastic portion 63 of the belt 61. This causes the two points 64, 65 defining the length of the elastic portion 63 of the belt 61 to increase in like manner. The wire 68 is pulled through the tube 66 and effects a linear translation of the radio-opaque marker 60. Reduction in the circumference of the patient's chest 62 likewise effects a linear translation of the radio-opaque marker 60 in the opposite direction. The radio-opaque marker 60 may be placed so that it is visible in the fluoroscopic image of the patient. Sequential images of the patient during several respiratory cycles are measured precisely by the movement of the marker 60. Software then captures the movement of the image 71 of the marker 60 in the fluoroscopic image to correlate the patient's breathing cycle to the sequential fluoroscopic images 91.

In 4DIGRT simulation, the displayed reference DRR and corresponding MLC is triggered by the respiratory phase 97. Similarly for RGIMRT, the MLC overlay is linked to the respiratory phase and duty cycle threshold. Once the dynamic MLC characteristics are accounted for, both 4DIGRT and RGIMRT can be simulated prior to delivery in order to ensure that the patient is positioned accurately and the treatment is delivered as planned.

The present invention incorporates live acquisition of high quality fluoroscopic images (1024×1024), image intensifier distortion correction, breathing phase detection, reference DRRs and MLC display. The software can be run successfully on a Pentium IV 2.2 GHz computer with 1 G RAM. The system can successfully detect the breathing cycle and sequence the display and superposition of DRRs and dMLC. The complete simulation can be recorded at a rate of 30 frames per second for later review and analysis. With this system uncertainties in set-up and delivery of 4DIGRT and RGIMRT treatment can be greatly reduced. The recorded simulation provides information that could influence field design and plan development.

Figure 12:
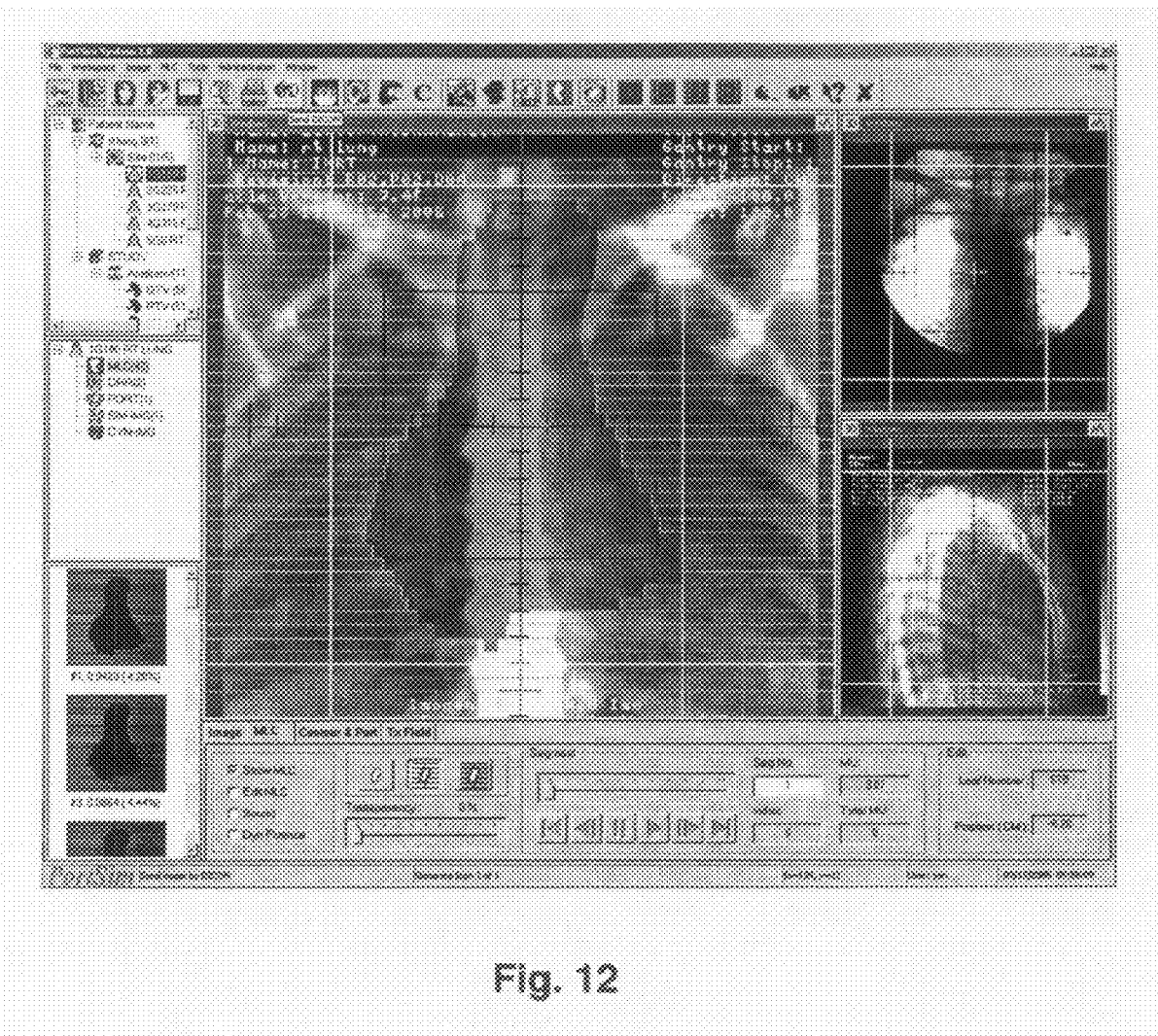
FIG. 12 is a view of a typical a graphic user interface in the Review Workspace.

To help setup the patient, reference images and contours are overlaid on the fluoroscopic image. A fast display engine in layered rendering technology accomplishes this task. When simulating beam-intensity modulation process, dynamic MLC segments are rendered in a realistic manner with leaf positions updated every 50 ms. FIG. 12 presents a typical layout of the graphic user interface of the present invention in the Review Workspace. In order to reduce the skin dose, usually only three to five respiration cycle fluoroscopic image sequences (10 to 20 seconds) is recorded for each field. When the simulation is reviewed, the image sequences may be displayed in cine mode to accommodate dynamic MLC segments.

The system allows the physician-physicist team to observe how 4DIGRT and RGIMRT are delivered to a moving target. By reviewing the recorded simulation, the treatment team is able to verify, or modify if necessary, the field position and margins so as to reduce the probability of underdosing the tumor or overdosing healthy tissues.

The system allows increased simulation throughput and provides a film-less environment for patient simulation and verification. The maximum image distortion correction error is less than 2 mm, making the digital images readily usable for review and planning purposes. Physician subjective error in reviewing films is significantly reduced due to the improved image quality and direct overlay of DRR and contours. The software allows for DICOM import and export to other devices, including printers. The systems significantly improves film review during the patient's treatment simulation. With features such as direct overlay, side-by-side display on the same screen and improved image quality, simulations can be performed more efficiently and more accurately. The simulation process can be recorded and provide valuable information for improving field design and patient immobilization techniques.

In some facilities, the final isocenter of a plan may be shifted from the initial isocenter marked in a virtual simulation system. It is usually verified in a conventional simulator by comparing reference DRR images with fluoroscopic images or simulation films. Human subjective error is one of the major sources of uncertainty in the isocenter verification (or simulation) process. The present invention addresses this problem by providing a dynamic treatment simulation system integrated with simulator to extend its functionalities.

FIG. 11 shows a typical display of the system. With the help of special rendering techniques, optimal display effect can be achieved by selecting individual rendering styles and object combinations. When simulating dynamic IMRT treatment, leaf dynamics are applied to calculating transit leaf positions (step-and-shot) or actual leaf positions (sliding window) to reflect MLC mechanical characteristics. Leaf positions are updated very 50 ms. In principle, every segment of an IMRT field can be verified online. Simulation processes can be recorded high resolution for later viewing and analysis.

The present invention has been described with reference to certain preferred and alternative embodiments that are intended to be exemplary only and not limiting to the full scope of the present invention as set forth in the appended claims.

What is claimed is:

1. A method for dynamic radiation therapy simulation of a treatment plan for a patient, comprising the steps of:
   storing on a computer readable medium a set of reference images of the patient,
   planning a multi-leaf collimator plan for dynamic radiation therapy for the patient comprising a sequence of plan images and storing said plan images on a computer readable medium;
   acquiring a sequence of real-time fluoroscopic images of the patient over at least one respiration cycle of the patient;
   correcting image intensifier distortion of said fluoroscopic images in real-time; and
   displaying the plan or reference images overlying the corrected fluoroscopic images in real-time;
   wherein a respiration cycle indicator indicates the respiratory cycle by changes in the circumference of the patient's chest; and
   wherein said respiration cycle indicator comprises a belt for encircling the patient's chest, said belt having an elastic portion extending between a first point and a second point on said belt; a tube having a first end in a fixed relationship to said first point; a flexible wire having a first end affixed to said second point, said wire passing through said tube and extending beyond a second end of said tube; a radio-opaque marker attached to a second end of said flexible wire whereby changes in circumference of the patient's chest effect a linear translation of said marker.

2. The method of claim 1 wherein said radio-opaque marker is imaged in said real-time fluoroscopic images.

3. The method of claim 2 wherein said plan images are gated to the respiratory cycle indicated by the radio-opaque marker.

4. The method of claim 1 wherein the step of correcting distortion of said fluoroscopic images in real-time comprises the steps of:
   compiling a library of correction models of image distortion for a plurality of image intensifier positions,
   capturing the position of the image intensifier for a fluoroscopic image;
   interpolating among adjacent image intensifier positions and calculating an interpolated correction model;
   preparing a two-dimensional indexing buffer from the interpolated correction model whereby each point in a corrected image is indexed to a point in the uncorrected image; and
   preparing a corrected image by selecting each corrected point from the uncorrected image as indexed by the indexing buffer.

* * * * *